United States Patent [19]

Mase et al.

[11] Patent Number: 4,507,394
[45] Date of Patent: Mar. 26, 1985

[54] HIGH ELECTRIC RESISTANT ZIRCONIA AND/OR HAFNIA CERAMICS

[75] Inventors: Syunzo Mase, Aichi; Shigeo Soejima, Nagoya, both of Japan

[73] Assignee: Ngk Insulators, Ltd., Japan

[21] Appl. No.: 559,269

[22] Filed: Dec. 8, 1983

[30] Foreign Application Priority Data

Dec. 24, 1982 [GB] United Kingdom ............... 8236813
Apr. 25, 1983 [GB] United Kingdom ............... 8311146

[51] Int. Cl.$^3$ .............................................. C04B 35/00
[52] U.S. Cl. ..................................... 501/94; 501/103; 501/134; 501/135
[58] Field of Search ................ 501/94, 103, 134, 135

[56] References Cited

U.S. PATENT DOCUMENTS 4,173,518 11/1979 Yamada et al. ................... 204/67
4,266,979 5/1981 Miyoshi et al. ................... 501/103
4,360,598 11/1982 Otagiri et al. ..................... 501/103

FOREIGN PATENT DOCUMENTS 58-55373 4/1983 Japan ................................. 501/103

Primary Examiner—Helen M. McCarthy
Attorney, Agent, or Firm—Parkhurst & Oliff

[57] ABSTRACT

Zirconia and/or hafnia-containing ceramics having high electric resistivity and mechanical strength which consists essentially of 5–30 mol % of at least one component of Group A consisting of $YO_{1.5}$, $ScO_{1.5}$, $SmO_{1.5}$, $EuO_{1.5}$, $GdO_{1.5}$, $TbO_{1.5}$, $DyO_{1.5}$, $HoO_{1.5}$, $ErO_{1.5}$, $TmO_{1.5}$, $YbO_{1.5}$, $LuO_{1.5}$, CaO and MgO, 5–40 mol % of at least one component of Group B consisting of $NbO_{2.5}$ and $TaO_{2.5}$ and 30–90 mol % of at least one component of Group C consisting of $ZrO_2$ and $HfO_2$, said ceramics preferably satisfying the following equation $\Sigma\{(4-(\text{ion valence number of each component of Group A}))\times(\text{number of mole of each component of Group A})\} \leq (\text{total number of mole of components of Group B})$.

and crystal phase of said ceramics being preferred to be composed mainly of tetragonal phase.

3 Claims, 3 Drawing Figures

FIG_1

HIGH ELECTRIC RESISTANT ZIRCONIA AND/OR HAFNIA CERAMICS

BACKGROUND OF THE INVENTION

1. Field of the Invention

The present invention relates to zirconia and/or hafnia-containing ceramics, particularly ceramics having a high electric resistance and ceramics having a high mechanical strength.

2. Description of the Prior Art

Heretofore, a variety of studies have been made with respect to ceramics consisting mainly of zirconia from both views of the functional materials and the constructive materials as solid electrolytes, parts having mechanical high strength and the like. In particular, when zirconia ceramics are used as a solid electrolyte, the internal resistance of a cell is preferred to be low in order to take out the electromotive force as an oxygen concentration cell and such ceramics that an electric resistance is as low as possible at a high temperature range of higher than about 350° C., have been used. In these ceramics, the high mechanical strength has been demanded in order to improve the vibration resistance and the thermal shock resistance.

Embodiments of such zirconia ceramics are disclosed in U.S. Pat. No. 4,266,979, U.S. Pat. No. 4,360,598 and Japanese Patent Laid-Open Application No. 58-55,373.

The reason why zirconia ceramics can be used as a solid electrolyte is due to oxygen ion vacancy caused by addition of a stabilizer such as $Y_2O_3$, CaO and the like to $ZrO_2$ as well known. That is, when the position $Zr^{4+}$ of positive tetravalent ion is substituted with $Y^{3+}$ or $Ca^{2+}$ of positive trivalent or divalent ion, the positive ion valence number per crystal lattice is reduced, so that the number of oxygen ion $O^{2-}$ having negative ion is reduced for maintaining the electric neutrality and the movement of oxygen ion becomes feasible due to oxygen ion vacancy caused therefrom.

The concentration cell constructed with such a theory is reversible and if there is difference of the oxygen concentration between both ends of the solid electrolyte, the electromotive force is caused by the well known Nernst's equation $$E = \frac{RT}{4F} \ln \frac{P_{O_2}(I)}{P_{O_2}(II)}$$

and reversely, when a direct current voltage is applied to both ends of the solid electrolyte to flow current, oxygen ion moves from negative direction toward positive direction and oxygen can be moved from one side of the solid electrolyte to another side. This is well known as oxygen pump.

When a direct current voltage is applied to conventional zirconia ceramics to flow current, if the applied voltage is lower than 1 V, the movement of the oxygen ion occurs moderately, so that an oxygen pump is obtained but when the applied voltage is higher and becomes about 10 V, the movement of oxygen ion can not flow to the direct current and polarization occurs in the interior of zirconia ceramics and oxygen ion in the negative side is deficient and zirconia ceramics is broken down.

Namely, the prior zirconia ceramics have been very weak against the application of the direct current voltage.

When such zirconia ceramics are used as a solid electrolyte for an oxygen sensor, the drawbacks appear in the following case.

In particular, when zirconia ceramics are used as an oxygen sensor for automotive exhaust gas, in order to operate the sensor at the exhaust gas temperature of as low as about 350° C., the portion constructing the concentration cell is heated with a heater. This structure is shown, for example, in U.S. Pat. No. 4,334,974. In the oxygen sensor having such a structure, the heater is heated at a direct current voltage of about 12–14 V which is battery voltage and therefore an insulating layer must be interposed between the heater and the concentration cell in order that the voltage for heating the heater does not influence upon the electromotive force of the concentration cell. If a conventional zirconia ceramics is used as this insulating layer, the zirconia ceramics is not only broken by the direct current voltage of 12–14 V applied to the heater, but also the voltage applied to the heater influences upon the electromotive force of the concentration cell due to zirconia of which the electric resistance becomes lower at a high temperature. When alumina ceramics which is a high resistor as an insulating layer, is used, the insulating property is good but said ceramics are different from zirconia ceramics constructing the concentration cell in the thermal expansion coefficient, so that in the use when the heat cycle between a high temperature and a low temperature is vigorous, alumina ceramics is exfoliated from the concentration cell composed of zirconia ceramics. Furthermore, such an oxygen sensor has a drawback that in the production, when zirconia and alumina which are different in the firing shrinkage percent, are co-fired, zirconia and alumina are exfoliated upon firing and cooling.

SUMMARY OF THE INVENTION

The present invention has been made for solving the above described drawbacks and aims to obtain ceramics having substantially the same firing shrinkage and thermal expansion properties with conventional zirconia ceramics, a high electric resistivity, that is a satisfactory direct current voltage resistance and a high mechanical strength.

DESCRIPTION OF THE PREFERRED EMBODIMENTS

The present invention lies in ceramics consisting essentially of 5–30 mol% of at least one component selected from Group A consisting of $YO_{1.5}$, $ScO_{1.5}$, $SmO_{1.5}$, $EuO_{1.5}$, $GdO_{1.5}$, $TbO_{1.5}$, $DyO_{1.5}$, $HoO_{1.5}$, $ErO_{1.5}$, $TmO_{1.5}$, $YbO_{1.5}$, $LuO_{1.5}$, CaO and MgO, 5–40 mol% of at least one component selected from Group B consisting of $NbO_{2.5}$ and $TaO_{2.5}$ and 30–90 mol% of at least one component selected from Group C consisting of $ZrO_2$ and $HfO_2$, the composition preferably satisfying the following equation Σ{(ion 4−(valence number of ion of each component of Group A))×(number of mole of each component of Group A)}≦(total number of mole of components of Group B)
and the crystal phase is preferably mainly tetragonal.

The present invention will be explained in more detail.

In the prior zirconia ceramics, only components belonging to Group A defined in the present invention, such as yttria, calcia, magnesia and the like are added as the stabilizer. Of course, there are embodiments wherein a sintering aid somewhat is added thereto but the sintering aid has substantially no relation to the stabilization of zirconia ceramics. Therefore, the prior zirconia ceramics have a large number of oxygen ion vacancies in the crystal lattice as mentioned above.

While, the present invention is characterized in that the amount of oxygen ion vacancy is reduced by adding the components belonging to Group B, that is components which become pentavalent positive ions, other than the stabilizer belonging to Group A. For example, if equimolar number of $YO_{1.5}$ and $NbO_{2.5}$ are added to $ZrO_2$, both $YO_{1.5}$ and $NbO_{2.5}$ form a solid solution together with $ZrO_2$ in the crystal and $Y^{3+}$ ion and $Nb^{5+}$ ion are formed other than $Zr^{4+}$ ion. In this case, $Y^{3+}$ ion and $Nb^{5+}$ ion are equimolar number, so that these ions become tetravalent positive ion in average and therefore become the same electric charge as $Zr^{4+}$ ion and $O^{2-}$ ion in the crystal lattice can maintain the electric neutrality in the amount of the stoichiometric volume of $ZrO_2$, so that $O^{2-}$ ion vacancy is not substantially caused. Accordingly, $O^{2-}$ ion hardly moves in the crystal and ceramics having an electrically high resistance are formed.

Figure 1:
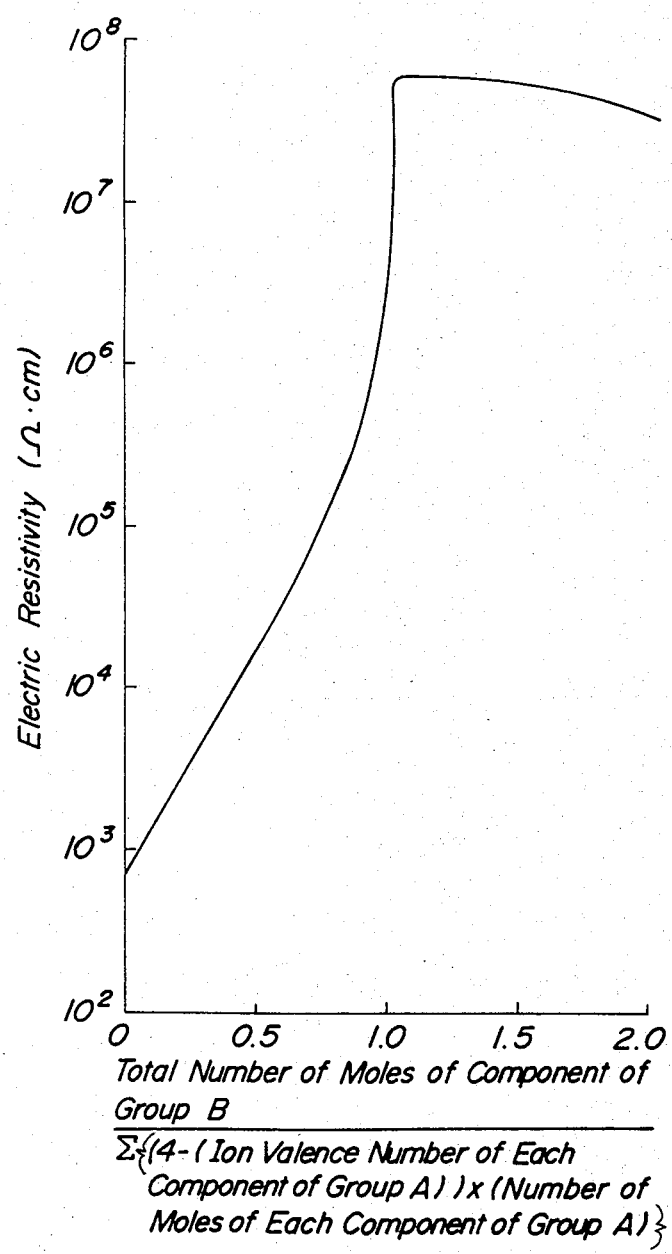
FIG. 1 is a graph illustrating the variation of electric resistivity when the mixed ratio of the components of Group A and the components of Group B is varied.

As conceived from the above theory, even if the number of moles of the components of Group B which become pentavalent positive ion is less than the number of moles of the components of Group A which become divalent or trivalent positive ion, the addition of the components of Group B has the effect that the oxygen ion vacancy in the ceramics is reduced and the electric resistivity of the ceramics is enhanced but when the number of mole of the components of Group B becomes larger and the oxygen ion vacancy in the ceramics is not substantially caused, the electric resistivity is considerably increased. FIG. 1 shows the variation of the electric resistivity of ceramics when the ratio of (total number of mole of components of Group B)/Σ{(4−(ion valence number of each component of Group A))×(number of mole of each component of Group A)} is varied. The measurement temperature was 600° C.

As seen from FIG. 1, when said ratio assumes the following relation, the electric resistivity suddenly increases and a desirable ceramic is obtained, Σ{(4−(ion valence number of each component of Group A))×(number of mole of each component of Group A)}≦(total number of mole of components of Group B). Furthermore, FIG. 1 shows the average value of the electric resistivity of ceramics obtained by various combinations of the present invention.

The components of each of Groups A, B and C are selected by the following reason. Any components shown in Group A can be utilized even in one component as the stabilizer of $ZrO_2$ or $HfO_2$. This has been well known.

The components shown in Group B are added in order to reduce the oxygen ion vacancy and increase the electric resistivity. Therefore, any components which become positive ions of five or more valence, are active but in order to form a solid solution together with $ZrO_2$ or $HfO_2$, the components must have a given ion radius and as the results of a large number of experiments, $NbO_{2.5}$ and $TaO_{2.5}$ are most effective. The selection of these two components is a characteristic of the present invention. The elements shown in Group C are selected so that the same thermal expansion property as the prior zirconia ceramics is obtained. It has been well known that $ZrO_2$ and $HfO_2$ are similar in various properties and the same effects have been obtained in the experiments by which the present invention has been accomplished.

The composition range of each group has been determined by the following reasons.

The components shown in each of Group A and Group B have no activity to the stabilization of $ZrO_2$ and/or $HfO_2$ against the components of Group C in an addition amount of less than 5 mol%. In only the components of Group A, $ZrO_2$ and/or $HfO_2$ can be stabilized in the crystal phase containing tetragonal or cubic phase, in some cases monoclinic phase in the addition of more than 4 mol% but in only the components of Group B, these components have no activity for stabilizing $ZrO_2$ and/or $HfO_2$. However, if both the components of Group A and Group B are added in an amount of at least 5 mol% respectively, $ZrO_2$ and/or $HfO_2$ are stabilized and the ceramics having a high resistance can be obtained.

The term "stabilization of $ZrO_2$ and/or $HfO_2$" used herein means that the formation of monoclinic phase is limited or the monoclinic phase is not formed as in so-called "partially stabilized zirconia" or "full stabilized zirconia".

When more than 30 mol% of the components of Group A and more than 40 mol% of Group B are concurrently added to the components of Group C, the phase which is presumed to be a compound consisting of the components of Group A and the components of Group B, increases and the thermal expansion coefficient lowers and the mechanical strength is reduced and such amounts are not desirable.

In the crystal phase of the ceramics of the present invention, there is either a tetragonal, cubic or monoclinic crystal phase, or mixed phases thereof, but the crystal phase shows different behavior from the case where only the stabilizer belonging to Group A is added to $ZrO_2$ as in the prior arts.

According to $ZrO_2$-$YO_{1.5}$ system phase diagram (for example, H. G. Scott, Journal of Materials Science, 10(1975), 1527–1535), if a solid solution having a composition of more than 15 mol% of $YO_{1.5}$ and a balance of $ZrO_2$ is formed, the product is substantially composed of cubic phase. However, in the present invention, for example, if a solid solution having a composition of 17 mol% of $YO_{1.5}$ and 18 mol% of $NbO_{2.5}$ and a balance of $ZrO_2$ is formed, the ceramics consists mainly of a tetragonal phase and in addition, a monoclinic phase and a compound phase presumed to be formed by reacting $YO_{1.5}$ with $NbO_{2.5}$ may be slightly precipitated.

The crystal phase of the ceramics in the case of other compositions of the present invention, when the amount of mole of components of Group B is smaller than that of the components of Group A, becomes cubic, tetragonal or the mixed phase thereof but when the amount of mole of the components of Group B is larger than that of the components of Group A, a tetragonal phase becomes the main part and in some cases, a monoclinic phase and a phase (referred to as "X phase" hereinafter) presumed to be a compound phase of the components of Group A and the components of Group B are precipitated.

The crystal phase of the ceramics of the present invention, even in ceramics having the given composition, varies according to the combination of various factors, for example, the crystal grain size of the starting material, mixing process of the components of each group, the firing condition and the like.

Even in the case of any crystal phase, the electric resistivity is similarly higher than the prior zirconia ceramics but when the amount of monoclinic phase becomes larger, if such ceramics is left to stand at a temperature range of about 250° C. for a long time, the ceramics are apt to be deteriorated and when the amount of X phase becomes larger, the electric resistivity somewhat lowers and also the flexural strength of the ceramics lowers and these cases are not desirable. Thus, the crystal phase of the ceramics of the present invention preferably consists mainly of a tetragonal phase. The term "consisting mainly of a tetragonal phase" used herein, shows that the height of the strongest peak of the tetragonal phase is highest, when the heights of the strongest peaks of every phase inspected by x-ray diffraction of the ceramics are compared.

Figure 2:
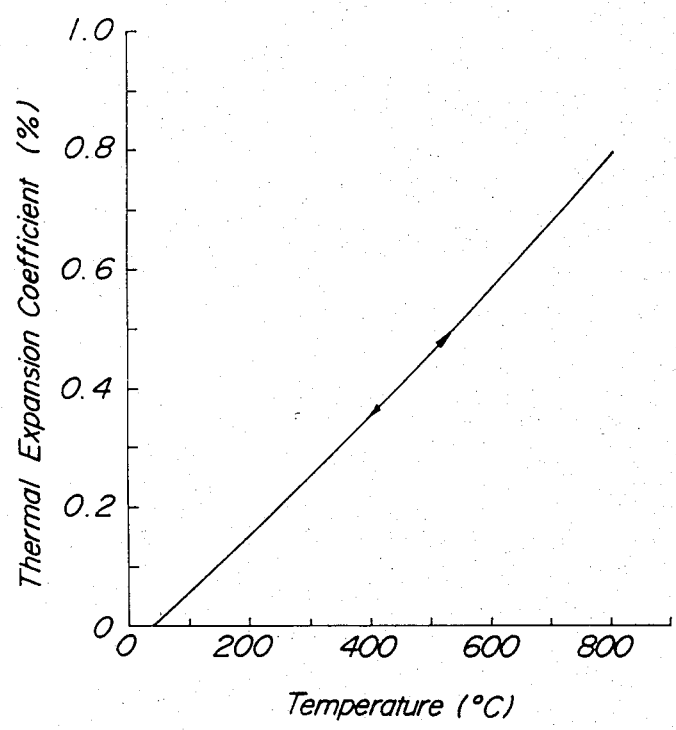
FIG. 2 is a graph illustrating the thermal expansion property of ceramics of the present invention.

The thermal expansion coefficient of the ceramics obtained in the present invention varies linearly both when the temperature is raised from room temperature to 800° C. or decreases from 800° C. to room temperature, as one embodiment is shown in FIG. 2 and there is no hysteresis due to the phase transformation and the like. The thermal expansion coefficient thereof is $0.9 \sim 1.1 \times 10^{-5}$ ° C.$^{-1}$ and is not substantially different from $1.0 \sim 1.1 \times 10^{-5}$ ° C.$^{-1}$ of the prior stabilized zirconia ceramics.

The sample in FIG. 2 is the composition of 20 mol% of $YO_{1.5}$, 21 mol% of $TaO_{2.5}$ and 59 mol% of $ZrO_2$ but even in other compositions of the present invention, the behavior is not varied.

Of course, there is no great difference in the ceramic thermal expansion coefficient wherein the crystal phase consists mainly of a tetragonal phase and the ceramics wherein the crystal phase consists mainly of a cubic phase.

When the prior zirconia ceramics containing tetragonal phase are left to stand at a temperature range of 200° C.$\sim$300° C. for a long time, said ceramics are sometimes deteriorated and broken. While, even when the ceramics of the present invention are left to stand at a temperature range of 200° C.$\sim$300° C. for more than 1,000 hours, the ceramics are neither broken nor cause significant variation in the electric resistivity, flexural strength and thermal expansion coefficient.

The ceramics of the present invention can be produced as follows.

Firstly, the components of each of Group A, Group B and Group C are mixed in the given amounts. The starting material containing these components may be powdery oxides or other compounds which are converted into oxides through thermal decomposition. When the powdery oxides are used as the starting material, when the average grain size of the powders is less than 1 μm, the mixing is easy and such starting material is preferable.

As the case may be, it is preferable to effect the mixing in a wet process. When the mixing is effected by a wet process, after mixing, the mixture is thoroughly dried. Then, if necessary, the mixture is calcined. This calcination, when the starting material being not oxides is used, has the effect, by which the starting material is converted into oxides and when only the starting material of oxides is used, the calcination has the effect for promoting the mixing of the starting material. The calcining temperature may be an optional temperature of about 400°$\sim$1,200° C.

Then, the mixture is pulverized, when the mixture is solidified by the calcination and the like, the mixture is preferably coarsely crushed by a mortar, roll crusher and the like. The pulverizing is carried out by a ball mill and the like. Anyone of wet-pulverizing and dry-pulverizing may be used but the dry-pulverizing using a ball mill, a vibration mill and the like is preferable. The dry-pulverizing has the effects that the pulverizing time is short, the firing temperature is low, the firing shrinkage percent is reduced and the like, and the components of Group A, the components of Group B and the components of Group C are mixed thoroughly and the solid solution is readily formed. As a result, ceramics having a high electric resistivity can be easily obtained.

Then, the obtained powders are shaped with a press, slip cast and the like and fired. The firing temperature is preferred to be a temperature range of 1,000°$\sim$1,600° C. The firing atmosphere may be any of air, oxidizing atmosphere and reducing atmosphere. In the reducing atmosphere, oxygen in the sintered body is taken off and the product may become blackish but thereafter if the sintered body is annealed in air, the blackening can be simply eliminated. The firing may be effected by a hot press and the like.

In the present invention, clay, alumina, glass, etc. may be contained in an amount of less than about 30% by weight as a sintering aid in addition to the components listed as the above described Group A, Group B and Group C. In particular, when the amount of mole of the components of Group B is larger than that of the components of Group A, breakage may be caused upon firing but this can be solved by the addition of the sintering aid. These substances do not particularly noticeably affect the electric resistivity. However, when the addition is excessive, the firing shrinkage percent upon the production and the thermal expansion coefficient of the ceramics vary, so that any amount exceeding about 30% by weight is not preferable.

Furthermore, the usual $ZrO_2$ starting material contains about 1-2% by weight of $HfO_2$, "$ZrO_2$" referred to in the present invention contains this amount of $HfO_2$ and when the description of "mixing of $ZrO_2$ and $HfO_2$" used herein means the mixture of $ZrO_2$ containing a slight amount of $HfO_2$ with purified $HfO_2$. However, examination has been made with respect to $ZrO_2$ having a high purity in which the content of $HfO_2$ is less than 100 ppm and of course, $ZrO_2$ starting material having a high purity may be used.

Various properties used in the present invention were determined as follows.

The measurement of the electric resistivity was as follows. On both surfaces of a disc-shaped ceramics having a diameter of more than 20 mm and a thickness of about 1 mm, were formed electrodes and such ceramics were put in an electric furnace of air atmosphere and the electric resistivity was measured by a direct current two terminal process. The measuring temperature was 600° C. and the applied voltage was 0.1-50 V.

The crystal phase was measured as follows. Polished mirror faces of disc-shaped ceramics having a diameter of about 15 mm and a thickness of about 3 mm were measured with an x-ray diffractometer.

The flexural strength was measured as follows. A rod-shaped (3×4×40 mm) and chamfered ceramic was used and the flexural strength of the ceramic was measured by four point bending process of an external span of 30 mm, an internal span of 10 mm and a cross head speed of 0.5 mm/min.

The thermal expansion coefficient was measured by using a rod-shaped (4×4×50 mm) ceramic and by means of a differential expansion meter in which quartz glass is a standard.

The following examples are given for the purpose of illustration of this invention and are not intended as limitations thereof.

EXAMPLE 1

A mixture consisting of zirconium oxide powder or hafnium oxide powder, powder of an oxide consisting of the component of Group A or a compound for example, yttrium nitrate, which is formed into the component of Group A through thermal decomposition, and powder consisting of the component of Group B in a mixing ratio shown in the following Table 1 was calcined at 800° C. After the calcination, the calcined product was mixed with a sintering aid in the case when a sintering aid shown in Table 1 was to be added, and then mixed with 0.5% by weight of polyethyleneglycol stearate as a pulverizing aid, and the resulting mixture was pulverized in a dry state for 20–200 hours. The resulting powder was press molded and then fired at 1,250°–1,400° C. The electric resistivity of the resulting sintered body was measured. The obtained results are shown in Table 1. It can be seen from Table 1 that the electric resistivity of the ceramics of Sample Nos. 1–19, which contain the component of Group B according to the present invention, is higher by as high as about $10^2 \sim 10^5$ Ω.cm than that of the ceramics of Sample No. 20, which does not contain the component of Group B.

TABLE 1(a)

| | Composition | | | | | | | | |
|---|---|---|---|---|---|---|---|---|---|
| | Group A | | | | Group B | | | | |
| Sample No. | Component | Mol % | Component | Mol % | Total mol % of Group A component | Component | Mol % | Component | Mol % | Total mol % of Group B component |
| 1 | $YO_{1.5}$ | 5 | | | 5 | $TaO_{2.5}$ | 5 | | | 5 |
| 2 | $YO_{1.5}$ | 6 | | | 6 | $NbO_{2.5}$ | 7 | | | 7 |
| 3 | $YO_{1.5}$ | 10 | | | 10 | $TaO_{2.5}$ | 8 | | | 8 |
| 4 | $YO_{1.5}$ | 15 | | | 15 | $NbO_{2.5}$ | 16 | | | 16 |
| 5 | $YO_{1.5}$ | 18 | | | 18 | $NbO_{2.5}$ | 20 | | | 20 |
| 6 | $YO_{1.5}$ | 18 | | | 18 | $TaO_{2.5}$ | 20 | | | 20 |
| 7 | $YO_{1.5}$ | 20 | | | 20 | $TaO_{2.5}$ | 15 | | | 15 |
| 8 | $YO_{1.5}$ | 20 | | | 20 | $NbO_{2.5}$ | 11 | $TaO_{2.5}$ | 11 | 22 |
| 9 | $YO_{1.5}$ | 20 | | | 20 | $NbO_{2.5}$ | 30 | | | 30 |
| 10 | $YO_{1.5}$ | 28 | | | 28 | $TaO_{2.5}$ | 30 | | | 30 |
| 11 | $YO_{1.5}$ | 30 | | | 30 | $NbO_{2.5}$ | 28 | | | 28 |
| 12 | $YO_{1.5}$ | 10 | $YbO_{1.5}$ | 10 | 20 | $NbO_{2.5}$ | 11 | $TaO_{2.5}$ | 11 | 22 |
| 13 | $SmO_{1.5}$ | 15 | | | 15 | $NbO_{2.5}$ | 16 | | | 16 |
| 14 | CaO | 15 | | | 15 | $NbO_{2.5}$ | 32 | | | 32 |
| 15 | MgO | 18 | | | 18 | $TaO_{2.5}$ | 40 | | | 40 |
| 16 | $YO_{1.5}$ | 10 | $ErO_{1.5}$ | 10 | 20 | $NbO_{2.5}$ | 10 | $IaO_{0.5}$ | 11 | 21 |
| 17 | $YO_{1.5}$ | 20 | | | 20 | $NbO_{2.5}$ | 21 | | | 21 |
| 18 | $YbO_{1.5}$ | 25 | | | 25 | $TaO_{2.5}$ | 28 | | | 28 |
| 19 | $YO_{1.5}$ | 30 | | | 30 | $TaO_{2.5}$ | 35 | | | 35 |
| 20 | $YO_{1.5}$ | 20 | | | 20 | — | | | | |

TABLE 1(b)

| | Composition | | | | | | |
|---|---|---|---|---|---|---|---|
| | Group C | | | | | | |
| Sample No. | Component | Mol % | Component | Mol % | Total mol % of Group C component | Sintering aid[1] Compound | Wt. % | Electric resistivity (Ω · cm) |
| 1 | $ZrO_2$ | 90 | | | 90 | — | — | $7.6 \times 10^6$ |
| 2 | $ZrO_2$ | 87 | | | 87 | alumina | 3 | $3.8 \times 10^7$ |
| 3 | $ZrO_2$ | 82 | | | 82 | — | — | $1.2 \times 10^5$ |
| 4 | $ZrO_2$ | 69 | | | 69 | clay | 5 | $4.9 \times 10^7$ |
| 5 | $ZrO_2$ | 62 | | | 62 | clay | 2 | $5.2 \times 10^7$ |
| 6 | $ZrO_2$ | 62 | | | 62 | clay | 5 | $6.5 \times 10^7$ |
| 7 | $ZrO_2$ | 65 | | | 65 | alumina | 3 | $9.4 \times 10^4$ |
| 8 | $ZrO_2$ | 58 | | | 58 | alumina / silica | 5 / 5 | $7.1 \times 10^7$ |
| 9 | $ZrO_2$ | 50 | | | 50 | clay | 25 | $5.7 \times 10^7$ |
| 10 | $ZrO_2$ | 42 | | | 42 | — | — | $5.9 \times 10^7$ |
| 11 | $ZrO_2$ | 42 | | | 42 | — | — | $6.0 \times 10^5$ |
| 12 | $ZrO_2$ | 58 | | | 58 | — | — | $7.3 \times 10^7$ |
| 13 | $ZrO_2$ | 69 | | | 69 | alumina | 10 | $2.1 \times 10^7$ |
| 14 | $ZrO_2$ | 53 | | | 53 | silica | 5 | $2.0 \times 10^7$ |
| 15 | $ZrO_2$ | 42 | | | 42 | clay | 3 | $4.7 \times 10^7$ |
| 16 | $ZrO_2$ | 59 | | | 59 | clay | 5 | $6.2 \times 10^7$ |
| 17 | $ZrO_2$ | 30 | $HfO_2$ | 29 | 59 | alumina | 3 | $2.9 \times 10^7$ |

TABLE 1(b)-continued

| | Composition | | | | | | |
|---|---|---|---|---|---|---|---|
| | Group C | | | | Sintering aid[1] | | Electric resistivity ($\Omega \cdot$ cm) |
| Sample No. | Component | Mol % | Component | Mol % | Total mol % of Group C component | Compound | Wt. % | |
|---|---|---|---|---|---|---|---|---|
| 18 | $HfO_2$ | 47 | | | 47 | clay alumina | 5 5 | $3.2 \times 10^7$ |
| 19 | $ZrO_2$ | 35 | | | 35 | clay | 5 | $7.0 \times 10^7$ |
| 20 | $ZrO_2$ | 80 | | | 80 | — | — | $7.2 \times 10^2$ |

[1]Addition amount of sintering aid based on the total weight of ceramics.

EXAMPLE 2

The thermal expansion coefficient, flexural strength, main crystal phase of each ceramic obtained in Example 1 and shown in Table 1 were measured. The obtained results are shown in the following Table 2. It can be seen from Table 2 that the thermal expansion coefficient of ceramics of Sample Nos. 1–19 according to the present invention ranges from $0.9 \times 10^{-5}$° C.$^{-1}$ to $1.0 \times 10^{-5}$° C.$^{-1}$, and is different by only small value within $0.2 \times 10^{-5}$° C.$^{-1}$ from that of $1.1 \times 10^{-5}$° C.$^{-1}$ of conventional ceramic of Sample No. 20. While, the flexural strength of the ceramics of the present invention is higher than that of the conventional ceramic of Sample No. 20 by as high as not less than 2 times, and the ceramics of the present invention have a crystal phase consisting mainly of a cubic phase. The ceramics of Sample Nos. 1–20 were left to stand at 250° C. for 1,000 hours in the air to effect a durability test, and the electric resistivity, thermal expansion coefficient and flexural strength of the above treated ceramics were measured. As the results, it was found that all of these properties did not substantially change from the properties before the durability test as shown in Table 2. Further, a disc-shaped test piece was produced from each of these ceramics, and a durability test of the ceramics was effected by applying 15 V of DC current between both electrodes for 1,000 hours in an electric furnace kept at 800° C. As the result, it was found that the conventional ceramic of Sample No. 20 was broken, but the ceramics according to the present invention were not broken, and their electric resistivity did not substantially change from the electric resistivity before the application of the DC current.

TABLE 2

| | Before a durability test | | | | After a durability test at 250° C. for 1,000 hours | | | After a durability test by applying DC current at 800° C. for 1,000 hours |
|---|---|---|---|---|---|---|---|---|
| Sample No. | Thermal expansion coefficient ranging from 40° C. to 800° C. (°C.$^{-1}$) | Flexural strength (kg/mm$^2$) | Main[2] crystal phase | Electric resistivity ($\Omega \cdot$ cm) | Thermal expansion coefficient ranging from 40° C. to 800° C. (°C.$^{-1}$) | Flexural strength (kg/mm$^2$) | | Electric resisitivity ($\Omega \cdot$ cm) |
| 1 | $1.0 \times 10^{-5}$ | 33 | T | $7.8 \times 10^6$ | $1.0 \times 10^{-5}$ | 34 | | $8.5 \times 10^6$ |
| 2 | $1.0 \times 10^{-5}$ | 37 | T | $3.7 \times 10^7$ | $1.0 \times 10^{-5}$ | 40 | | $3.9 \times 10^7$ |
| 3 | $1.0 \times 10^{-5}$ | 34 | T | $1.3 \times 10^5$ | $1.0 \times 10^{-5}$ | 36 | | $3.0 \times 10^5$ |
| 4 | $1.0 \times 10^{-5}$ | 40 | T | $5.3 \times 10^7$ | $1.0 \times 10^{-5}$ | 41 | | $5.0 \times 10^7$ |
| 5 | $1.0 \times 10^{-5}$ | 45 | T | $5.1 \times 10^7$ | $1.0 \times 10^{-5}$ | 47 | | $5.3 \times 10^7$ |
| 6 | $1.0 \times 10^{-5}$ | 39 | T | $6.7 \times 10^7$ | $1.0 \times 10^{-5}$ | 39 | | $6.4 \times 10^7$ |
| 7 | $1.0 \times 10^{-5}$ | 33 | T | $9.3 \times 10^4$ | $1.0 \times 10^{-5}$ | 34 | | $2.1 \times 10^5$ |
| 8 | $1.0 \times 10^{-5}$ | 37 | T | $7.1 \times 10^7$ | $1.0 \times 10^{-5}$ | 39 | | $7.1 \times 10^7$ |
| 9 | $0.9 \times 10^{-5}$ | 30 | T | $5.7 \times 10^7$ | $0.9 \times 10^{-5}$ | 32 | | $5.8 \times 10^7$ |
| 10 | $1.0 \times 10^{-5}$ | 41 | T | $5.7 \times 10^7$ | $1.0 \times 10^{-5}$ | 42 | | $5.7 \times 10^7$ |
| 11 | $1.0 \times 10^{-5}$ | 23 | T + C | $6.2 \times 10^5$ | $1.0 \times 10^{-5}$ | 25 | | $1.3 \times 10^6$ |
| 12 | $1.0 \times 10^{-5}$ | 37 | T | $7.2 \times 10^7$ | $1.0 \times 10^{-5}$ | 37 | | $7.4 \times 10^7$ |
| 13 | $1.0 \times 10^{-5}$ | 29 | T | $2.4 \times 10^7$ | $1.0 \times 10^{-5}$ | 30 | | $2.2 \times 10^7$ |
| 14 | $1.0 \times 10^{-5}$ | 32 | T | $2.1 \times 10^7$ | $1.0 \times 10^{-5}$ | 32 | | $1.9 \times 10^7$ |
| 15 | $1.0 \times 10^{-5}$ | 32 | T | $4.9 \times 10^7$ | $1.0 \times 10^{-5}$ | 33 | | $5.0 \times 10^7$ |
| 16 | $1.0 \times 10^{-5}$ | 38 | T | $6.2 \times 10^7$ | $1.0 \times 10^{-5}$ | 40 | | $6.3 \times 10^7$ |
| 17 | $1.0 \times 10^{-5}$ | 31 | T | $2.8 \times 10^7$ | $1.0 \times 10^{-5}$ | 32 | | $2.8 \times 10^7$ |
| 18 | $1.0 \times 10^{-5}$ | 29 | T | $3.3 \times 10^7$ | $1.0 \times 10^{-5}$ | 31 | | $3.2 \times 10^7$ |
| 19 | $0.9 \times 10^{-5}$ | 34 | T + M | $7.1 \times 10^7$ | $0.9 \times 10^{-5}$ | 20 | | $7.1 \times 10^7$ |
| 20 | $1.1 \times 10^{-5}$ | 12 | C | $7.3 \times 10^2$ | $1.1 \times 10^{-5}$ | 11 | | broken |

[2]T: Tetragonal crystal.
C: Cubic crystal.
M: Monoclinic crystal.

EXAMPLE 3

Oxide powders of respective components or compounds, which would be formed into the oxides through thermal decomposition, were mixed in a wet state such that the resulting mixture had a composition shown in the following Table 3. After drying, the mixture was calcined at a temperature within the range of 600°–1,000° C. The calcined product was crushed, mixed with a sintering aid in the case where a sintering aid shown in Table 3 was to be added, and then subjected to pulverization, press molding and firing in the same manner as described in Example 1. In Table 3, Sample Nos. 21–32 are ceramics of the present invention, and Sample Nos. 33–36 are ceramics outside the scope of the present invention. The resulting ceramics were measured with respect to the electric resistivity, thermal expansion coefficient, flexural strength and crystal phase. The obtained results are shown in Table 3. It can be seen from Table 3 that all the electric resistivities of the ceramics are high and are in the order of $10^7 \Omega$.cm. While, the thermal expansion coefficients thereof are within the range of $0.9 \times 10^{-5}$° C.$^{-1} \sim 1.0 \times 10^{-5}$° C.$^{-1}$ and are substantially the same as those of conventional zirconia ceramics. The crystal phase of the ceramics of the present invention consists of tetragonal phase or a mixed phase of tetragonal phase and cubic phase.

solid electrolyte 1, whereby an oxygen concentration cell 8 is formed. Further, an insulating layer 9 is tightly adhered to the oxygen concentration cell 8, a heater 10 is arranged on the surface of the insulating layer 9, a TABLE 3(a)

| | Composition | | | | | | | | | |
|---|---|---|---|---|---|---|---|---|---|---|
| | Group A | | | | | | Group B | | | |
| Sample No. | Component | Mol % | Component | Mol % | Component | Mol % | Total mol % of Group A component | Component | Mol % | Component | Mol % | Total mol % of Group B component |
| 21 | $ScO_{1.5}$ | 15 | | | | | 15 | $TaO_{2.5}$ | 17 | | | 17 |
| 22 | $EuO_{1.5}$ | 10 | | | | | 10 | $NbO_{2.5}$ | 11 | | | 11 |
| 23 | $GdO_{1.5}$ | 20 | | | | | 20 | $TaO_{2.5}$ | 25 | | | 25 |
| 24 | $TbO_{1.5}$ | 10 | | | | | 10 | $TaO_{2.5}$ | 15 | | | 15 |
| 25 | $DyO_{1.5}$ | 20 | | | | | 20 | $NbO_{2.5}$ | 25 | | | 25 |
| 26 | $HoO_{1.5}$ | 15 | | | | | 15 | $NbO_{2.5}$ | 17 | | | 17 |
| 27 | $TmO_{1.5}$ | 15 | | | | | 15 | $TaO_{2.5}$ | 20 | | | 20 |
| 28 | $LuO_{1.5}$ | 20 | | | | | 20 | $NbO_{2.5}$ | 25 | | | 25 |
| 29 | $ErO_{1.5}$ | 20 | | | | | 20 | $NbO_{2.5}$ | 22 | | | 22 |
| 30 | $YO_{1.5}$ | 5 | $YbO_{1.5}$ | 5 | $EuO_{1.5}$ | 10 | 20 | $NbO_{2.5}$ | 11 | $TaO_{2.5}$ | 11 | 22 |
| 31 | $YO_{1.5}$ | 15 | CaO | 15 | | | 30 | $NbO_{2.5}$ | 20 | $TaO_{2.5}$ | 20 | 40 |
| 32 | $YO_{1.5}$ | 16 | | | | | 16 | $NbO_{2.5}$ | 18 | | | 18 |
| 33 | $YO_{1.5}$ | 3 | | | | | 3 | $NbO_{2.5}$ | 2 | | | 2 |
| 34 | — | | | | | | | $TaO_{2.5}$ | 10 | | | 10 |
| 35 | $YO_{1.5}$ | 40 | | | | | 40 | $NbO_{2.5}$ | 40 | | | 40 |
| 36 | $YO_{1.5}$ | 8 | | | | | 8 | — | | | | |

TABLE 3(b)

| | Composition | | | | | Sintering aid[1] | | Electric resistivity ($\Omega \cdot cm$) | Thermal expansion coefficient ranging from 40° C. to 800° C. (°C.$^{-1}$) | Flexural strength (kg/mm$^2$) | Main[2] crystal phase | Remarks |
|---|---|---|---|---|---|---|---|---|---|---|---|---|
| | Group C | | | | | | | | | | | |
| Sample No. | Component | Mol % | Component | Mol % | Total mol % of Group C component | Compound | Wt. % | | | | | |
| 21 | $ZrO_2$ | 68 | | | 68 | alumina | 2 | $9.9 \times 10^7$ | $1.0 \times 10^{-5}$ | 31 | T | |
| 22 | $ZrO_2$ | 79 | | | 79 | — | | $4.7 \times 10^7$ | $1.0 \times 10^{-5}$ | 32 | T | |
| 23 | $ZrO_2$ | 55 | | | 55 | clay | 2 | $5.0 \times 10^7$ | $1.0 \times 10^{-5}$ | 37 | T | |
| 24 | $ZrO_2$ | 75 | | | 75 | alumina | 5 | $4.4 \times 10^7$ | $1.0 \times 10^{-5}$ | 32 | T | |
| 25 | $ZrO_2$ | 55 | | | 55 | clay | 2 | $5.0 \times 10^7$ | $1.0 \times 10^{-5}$ | 37 | T | |
| 26 | $ZrO_2$ | 68 | | | 68 | clay | 3 | $7.6 \times 10^7$ | $1.0 \times 10^{-5}$ | 39 | T | |
| 27 | $ZrO_2$ | 65 | | | 65 | alumina | 5 | $8.1 \times 10^7$ | $1.0 \times 10^{-5}$ | 37 | T | |
| 28 | $ZrO_2$ | 55 | | | 55 | — | | $5.9 \times 10^7$ | $1.0 \times 10^{-5}$ | 37 | T | |
| 29 | $ZrO_2$ | 58 | | | 58 | — | | $6.3 \times 10^7$ | $1.0 \times 10^{-5}$ | 40 | T | |
| 30 | $ZrO_2$ | 30 | $HfO_2$ | 28 | 58 | clay | 10 | $9.6 \times 10^7$ | $1.0 \times 10^{-5}$ | 39 | T | |
| 31 | $ZrO_2$ | 30 | | | 30 | clay | 5 | $7.3 \times 10^7$ | $0.9 \times 10^{-5}$ | 29 | T | |
| 32 | $ZrO_2$[3] | 66 | | | 66 | — | | $6.0 \times 10^7$ | $1.0 \times 10^{-5}$ | 39 | T | |
| 33 | $ZrO_2$ | 96 | | | 96 | clay | 5 | measurement is impossible | measurement is impossible | measurement is impossible | measurement is impossible | broken during firing |
| 34 | $ZrO_2$ | 90 | | | 90 | clay | 5 | measurement is impossible | measurement is impossible | measurement is impossible | measurement is impossible | broken during firing |
| 35 | $ZrO_2$ | 20 | | | 20 | — | | $2.4 \times 10^7$ | $0.8 \times 10^{-5}$ | 19 | X | |
| 36 | $ZrO_2$ | 92 | | | 92 | — | | $1.2 \times 10^3$ | $1.0 \times 10^{-5}$ | 53 | T | |

[1] Addition amount of sintering aid based on the total weight of ceramics.
[2] T: Tetragonal phase.
X: Mixed phase of compounds of Group A component and Group B component.
[3] High purity $ZrO_2$ having an $HfO_2$ content of not higher than 100 ppm.

EXAMPLE 4

Figure 3:
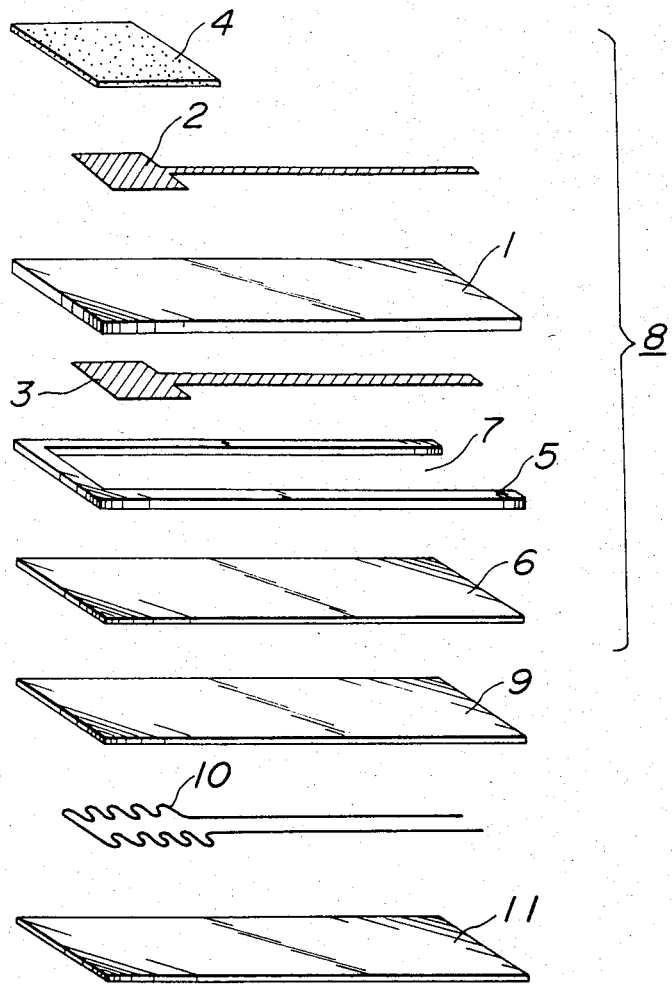
FIG. 3 is a view for illustrating the development of an oxygen sensor element produced in an example of the present invention.

Oxygen sensors were produced by using conventional zirconia ceramics and ceramics of the present invention. FIG. 3 shows the development of the sensors. In FIG. 3, a measuring electrode 2 is arranged on one surface of a solid electrolyte 1 consisting of zirconia ceramics, and a reference electrode 3 is arranged on another surface thereof. The measuring electrode 2 is contacted through a porous spinel layer 4 with a gas to be measured, and the reference electrode 3 is contacted with the air through a cavity 7 formed by a rectangular layer 5 and an airtight layer 6, both consisting of zirconia ceramics having the same composition as that of the protecting layer 11 is laminated so as to cover the heater 10 to form an oxygen sensor element. This oxygen sensor element was produced in the following manner.

Raw materials were mixed in a mixing ratio so as to form a mixture having the same composition as that of Sample No. 36 in Table 3, and the resulting mixture was treated according to the steps described in Example 1 to produce dried and pulverized zirconia powder. To 100 parts by weight of the dried and pulverized zirconia powder were added 8 parts by weight of polyvinylbutyral and 100 parts by weight of trichloroethylene, and the resulting mixture was homogeneously mixed for 16 hours in a ball mill to produce a zirconia slurry, and the zirconia slurry was spread into a plate-shaped article by a doctor blade method to produce a zirconia tape. An unfired zirconia plate, which would be made into a solid electrolyte 1, was cut out from this zirconia tape, and platinum paste to be formed into a reference electrode 3 was printed on one surface of the unfired zirconia plate. Further, unfired zirconia plates to be formed into a rectangular layer 5 and an airtight layer 6 were cut out from the same zirconia tape as the above described zirconia tape used for the production of the solid electrolyte 1, and laminated on the printed platinum paste under pressure. After lamination, a paste consisting of a powder having the same composition as that of Sample No. 5 described in Table 1 and used in the present invention was printed, so as to form an insulating layer 9, on one surface of the unfired zirconia plate to be formed into the airtight layer. After the resulting laminated mass was dried, a platinum paste to be formed into a heater 10 was printed on the printed layer to be formed into the insulating layer 9, and further the same paste as that used for the formation of the insulating layer 9 was printed on the above printed platinum paste in order to form a protecting layer 11. After the laminated assembly was fully dried, the resulting monolithically shaped article was fired at 1,350° C. in an electric furnace. After the firing, a measuring electrode 2 was formed on another surface of the solid electrolyte 1, on which the reference electrode 3 was not arranged, by a spattering of platinum, and a porous spinel layer 4 was plasma-coated on the spattered platinum of measuring electrode 2. The resulting oxygen sensor, wherein the ceramics of the present invention is used in the insulating layer 9 and protecting layer 11, is referred to as an oxygen sensor element A. For comparison, an oxygen sensor element B, wherein conventional zirconia ceramics having the same composition as that of the solid electrolyte 1 was used in the insulating layer 9 and protecting layer 11, and an oxygen sensor element C, wherein alumina ceramics was used in the insulating layer 9 and protecting layer 11, were produced. The solid electrolyte 1 of each oxygen sensor element had a dimension of 0.5 mm thickness, 6 mm width and 40 mm length. The oxygen sensor element A using the ceramics of the present invention and the oxygen sensor element B using the conventional zirconia ceramics did not bend during the firing, and were good in the adhesion between the airtight layer 6 and the insulating layer 9. However, the oxygen sensor element C, wherein the alumina ceramics was used, bent during the firing due to the difference of shrinkages during the firing between the zirconia ceramics, which formed the concentration cell 8, and the alumina ceramics, which formed the insulating layer 9 and protecting layer 11, and further somewhat cracked between the airtight layer 6 and the insulating layer 9.

Then, each oxygen sensor element was inserted into a propane gas burner while keeping such that air was introduced into the cavity 7, and the measuring electrode 2 was contacted with the burnt gas of propane, whereby an electromotive force caused between the measuring electrode 2 and the reference electrode 3 was measured in the following manner. Originally, the propane gas burner was controlled such that the temperature of burnt propane gas was 600° C., and electromotive forces of $E_R$ and $E_L$ at air/fuel ratios $\lambda$ of air/propane of $\lambda=0.9$ and $\lambda=1.1$ were measured. Then, the propane gas burner was controlled such that the temperature of the burnt propane gas was 300° C., and a DC current of 12 V was applied to the heater 10 to heat the oxygen sensor element, and then the electromotive forces $E_R$ and $E_L$ at $\lambda=0.9$ and $\lambda=1.1$ were measured. The consumed amount of electric power in the heater 10 was about 4 W in all oxygen sensor elements, and the temperature of the vicinity of the measuring electrode 2 rose to about 580° C. The result of the measurement of the electromotive forces is shown in the following Table 4. It can be seen from Table 4 that, when the oxygen sensor elements were not heated without applying the DC current to the heater 10, $E_R$ was 850–855 mV and $E_L$ was 48–50 mV in all oxygen sensor elements. When the oxygen sensor elements were heated by applying the DC current to the heater 10, the electromotive forces of $E_R$ and $E_L$ did not substantially change from the values before the DC current heating in the oxygen sensor element A wherein the ceramics of the present invention were used, and in the oxygen sensor element C wherein alumina ceramics were used, but the electromotive forces $E_R$ and $E_L$ of the oxygen sensor element B, wherein conventional zirconia ceramics were used, were increased and were about 500 mV higher than the values before the DC current heating.

Then, in each oxygen sensor element, when the application of the DC current of 12 V was further continued while exposing the oxygen sensor element to the burning gas of propane at 300° C., the electromotive force was no longer generated after about 10 minutes and the zirconia ceramic was broken in the oxygen sensor element B; on the contrary, in the oxygen sensor elements A and C, even after the lapse of time of 500 hours, the electromotive force properties did not change and the appearance of the sensor elements did not change as well.

When each oxygen sensor element was exposed to a heating-cooling cycle of about 100° C.⇌about 800° C. by the ignition and extinction of propane, there was no change in the oxygen sensor elements A and B even after 100 cycles; but in the oxygen sensor element C, after the lapse of 10 cycles, the zirconia ceramics which formed the airtight layer 6, peeled completely from alumina ceramics which formed the insulating layer 9.

TABLE 4

| Kind of oxygen sensor element | Without DC current heating | | After DC current heating | |
|---|---|---|---|---|
| | $E_R$ (mV) | $E_L$ (mV) | $E_R$ (mV) | $E_L$ (mV) |
| Oxygen sensor element A | 850 | 48 | 855 | 55 |
| Oxygen sensor element B | 855 | 50 | 1,350 | 560 |
| Oxygen sensor element C | 850 | 50 | 850 | 52 |

As described above, in spite of the fact the ceramics of the present invention have substantially the same thermal expansion property as that of the zirconia ceramics, the ceramics of the present invention have an electric resistivity higher than that of the zirconia ceramics by as high as $10^1 \sim 10^5$ $\Omega$.cm, is not broken even in the application of DC current, and can be used as an insulator. Moreover, the ceramics of the present invention have high mechanical strength and good durability over a wide temperature range. Accordingly, the ceramics of the present invention can be used as materials, which are required to have high mechanical strength and thermal stability, such as a structural material for internal combustion engine, cutting tool and the like, and further are very advantageous as materials which are laminated on zirconia ceramics used in a portion required to have electric insulating properties like oxygen sensors. Therefore, the present invention is very contributable for the development of the industry.

What is claimed is:

1. Ceramics which consist essentially of 5–30 mol% of at least one component of Group A consisting of $YO_{1.5}$, $ScO_{1.5}$, $SmO_{1.5}$, $EuO_{1.5}$, $GdO_{1.5}$, $TbO_{1.5}$, $DyO_{1.5}$, $HoO_{1.5}$, $ErO_{1.5}$, $TmO_{1.5}$, $YbO_{1.5}$, $LuO_{1.5}$, CaO and MgO, 5–40 mol% of at least one component of Group B consisting of $NbO_{2.5}$ and $TaO_{2.5}$ and 30–90 mol% of at least one component of Group C consisting of $ZrO_2$ and $HfO_2$.

2. Ceramics as claimed in claim 1, wherein said ceramics satisfy the following equation $\Sigma\{(4-$(ion valence number of each component of Group A))×(number of mole of each component of Group A)$\}\leq$(total number of mole of components of Group B).

3. Ceramics as claimed in claim 1, wherein a crystal phase present in said ceramics consists mainly of tetragonal phase.

* * * * *